(12) United States Patent
Bakke

(10) Patent No.: US 7,011,797 B2
(45) Date of Patent: Mar. 14, 2006

(54) APPARATUS FOR THAWING FROZEN BIOLOGICAL FLUIDS UTILIZING HEATING PLATES AND OSCILLATORY MOTION TO ENHANCE HEAT TRANSFER BY MIXING

(76) Inventor: Allan P Bakke, 3220 County View Ct. SW., Rochester, MN (US) 55902

( * ) Notice: Subject to any disclaimer, the term of this patent is extended or adjusted under 35 U.S.C. 154(b) by 307 days.

(21) Appl. No.: 10/611,747

(22) Filed: Jun. 30, 2003

(65) Prior Publication Data

US 2004/0265168 A1    Dec. 30, 2004

(51) Int. Cl.
*G01N 21/00* (2006.01)

(52) U.S. Cl. ............... 422/307; 219/200; 219/201; 219/245; 219/482; 422/62; 422/309; 604/903

(58) Field of Classification Search ............... 219/200, 219/201, 245, 482, 524; 604/903; 422/307, 422/309, 62

See application file for complete search history.

(56) References Cited

U.S. PATENT DOCUMENTS

| | | | | |
|---|---|---|---|---|
| 4,018,911 A | * | 4/1977 | Lionetti et al. | 424/533 |
| 4,486,389 A | | 12/1984 | Darnell | |
| 4,801,777 A | * | 1/1989 | Auerbach | 219/687 |
| 4,852,641 A | * | 8/1989 | Noble | 165/80.1 |
| 5,243,833 A | * | 9/1993 | Coelho et al. | 62/376 |
| 5,939,023 A | * | 8/1999 | Coelho et al. | 422/101 |
| 6,007,773 A | | 12/1999 | Kuzyk | |

\* cited by examiner

*Primary Examiner*—Krisanne Jastrzab

(57) ABSTRACT

An improved dry heat method and apparatus for thawing frozen biological fluids utilizing electrically heated plates and oscillatory motion to enhance heat transfer by mixing as the fluid thaws. Bags of frozen fluid to be thawed are lightly squeezed between two heating plates, one of which is gently oscillated to facilitate mixing of the thawing fluid, increasing heat transfer and reducing time required for thawing. Direct contact of the heating plates against the bag surfaces increases heat transfer by eliminating insulative effects of another bag wall and a water boundary layer, compared to water bath units. Flat (or curved to conform to bag) heat pipes are preferred as heating plates compared to plain aluminum sheet. Flat heat pipes have the property of an isothermal heating surface, thus maximizing heat transfer to the coldest areas, preventing hot spots, and simplifying heating plate temperature control.

15 Claims, 4 Drawing Sheets

APPARATUS FOR THAWING FROZEN BIOLOGICAL FLUIDS UTILIZING HEATING PLATES AND OSCILLATORY MOTION TO ENHANCE HEAT TRANSFER BY MIXING

BACKGROUND

1. Field of Invention

This invention relates to an improved apparatus and method of thawing frozen blood, blood plasma, or other temperature sensitive biological fluids. Storing blood plasma in the frozen state and thawing it as needed is a common practice in hospitals and blood banks. Because plasma or blood can only be used for a relatively short time after thawing, it is thawed in response to a specific patient's need. The need for such blood products is often urgent, making it important to thaw blood products rapidly but without overheating to prevent damage to the fluid during the thawing process.

2. Description of Prior Art

For a number of years it was common practice to thaw frozen plasma for use by placing the bag directly into a controlled temperature warm water bath, sometimes with agitaion of the water to increase heat transfer. More recently that method has been abandoned because of the possibility of contamination of the water bath with bacteria or other hazardous materials, which in turn could contaminate the access ports of the plasma bag. When the bag is accessed by an intravenous system component, the contaminant might be passed on to the patient receiving the transfusion.

U.S. Pat. No. 6,007,773 discloses a system for thawing blood plasma in which the plasma bag is first inserted into a thin waterproof bag and then immersed in a warm water bath. The outer bag, open on top and vented to atmosphere, isolates the plasma bag from contamination while adding some thermal resistance to convective warming of the plasma bag. Actively generated water currents exert a kneading effect on the thawing plasma bag to increase heat transfer.

While the technique previously described improved upon earlier methods, the need remains for a frozen plasma thawing system which can safely further reduce thawing time.

Although the current water bath method protects against contamination and employs water currents to increase convective warming, heating rates to the plasma bag are unnecessarily limited by thermal resistance in the added thin isolating bag and the water boundary layer outside the thawing bag.

SUMMARY

In accordance with a preferred embodiment of the invention, there is disclosed apparatus for thawing frozen biological fluids utilizing heating plates and oscillatory motion to enhance heat transfer. The plastic bag(s) containing frozen fluid to be thawed are gently held under light pressure between two parallel heating plates. The heating plates are preferably heat pipes, either flat or contoured to approximate the shape of the bag(s) being thawed. The heating plates are electrically heated by etched foil or other resistance heaters applied to their back surfaces, and the heating plate front heating surface temperature is controlled by a temperature controller utilizing thermistors or other sensors located on or near the heating surfaces. During thawing, one of the heating plates is oscillated in a direction perpendicular to its surface, relative to the other heating plate. The thawing fluid, within its bag, is thereby mixed, enhancing heat transfer and reducing thawing time. Means for maintaining the light squeezing pressure as the bag becomes thinner during thawing are disclosed, as are means for maintaining contact with the bag and for limiting the oscillating force during oscillation. Means for accommodating bags of different thicknesses are disclosed, and up to several bags may be thawed simultaneously. Completion of thawing is determined by a thermistor or other sensor in contact with the bag surface, but insulated from the heating plate.

The improvements of this invention provide the benefit of reduced thawing time through direct contact, conductive heat exchange utilizing flat heat pipes, while totally eliminating the use of a water bath and the potential for bacterial contamination from the water.

OBJECTS AND ADVANTAGES

Accordingly, several objects and advantages of my invention are as follows. The primary object of the invention is to provide a thawing device that utilizes flat heating plates which can thaw frozen fluids in significantly less time than current water bath devices require. Conductive heating directly from heating plates through the frozen fluid's bag wall eliminates the thermal resistance of the wall of the plastic bag used to isolate the thawing bag from the water bath. It also eliminates the significant convective thermal resistance of the water boundary layer of the water bath, increasing heat transfer to the thawing bag and reducing thawing time.

Heat pipes, either flat or contoured to approximate the shape of bags to be thawed, are preferred as heating plates. They are heated by etched foil or other resistance heaters applied to their back surfaces, and are maintained at a safe thawing temperature by an electronic temperature controller and sensors mounted at or near the heating surfaces of the heating plates. A sensor in thermal contact with a thawing bag but insulated from the heating plate is used to determine when thawing is complete. Heat pipe properties of maintaining an isothermal heating surface, delivering highest heat flux to the coldest region of the heating surface, and avoiding hot spots which may damage blood or sensitive biological fluids make them well-suited for this application.

Conductive heat transfer through dry heating plates also eliminates the contamination hazards associated with the use of water baths, and the attendant attempts to maintain asepsis of the baths.

By gently squeezing the bags being thawed between the two heating plates, contact surface area for heat transfer is increased as the bag contents partially thaw and the bag becomes thinner. Heat transfer to the thawing bags is also enhanced and increased by gently oscillating one heating plate relative to the other heating plate in a direction perpendicular to the heating surface, by promoting mixing of the liquid phase in the partially thawed bags.

Up to several bags may be thawed simultaneously between the heating plates of one apparatus, and bags of varying thickness are easily accommodated.

Still further objects and advantages will become apparent from a consideration of the ensuing description and accompanying drawings.

Figure 1:
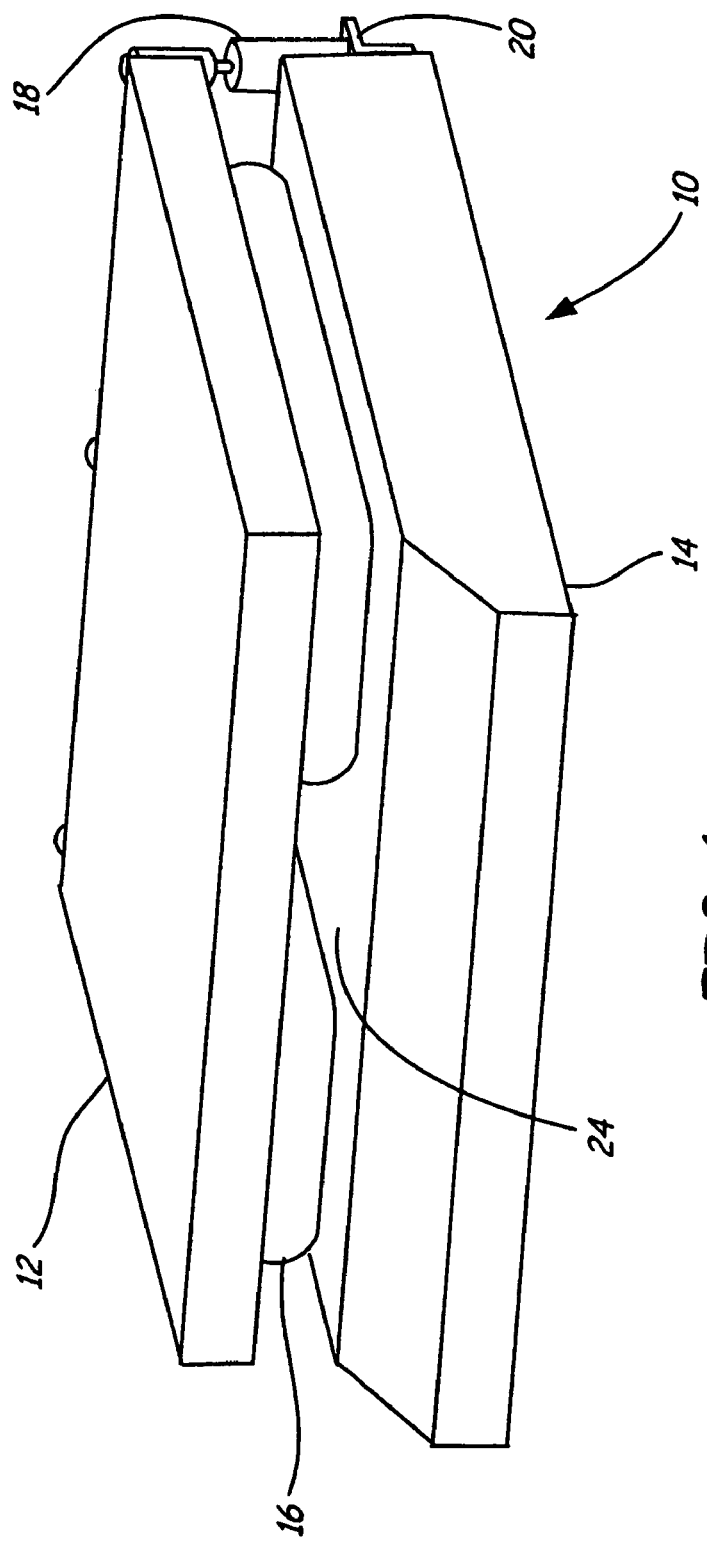
FIG. 1 is a perspective view of the invention from the front.

REFERENCE NUMERALS 10 thawing apparatus invention
12 top case
14 bottom case
16 bags
18 hinge supports
20 adjustable hinge mount
22 clevis and bracket assembly
24 heating plates
26 gearmotor
28 crankshaft
30 spring-dashpot
50 hanging bag embodiment
52 base
54 fixed case
56 movable case
58 bag hanging posts
60 latch
62 opening handle
64 rear heating plate
66 front heating plate
68 flexural support
70 spring-loaded supports
72 oscillating crank
74 spring-dashpot module
76 bellcrank
78 support rails
80 movable case slider
82 constant force return spring
84 oscillating gearmotor
86 mounting bracket

PREFERRED EMBODIMENT—DESCRIPTION

Figure 2:
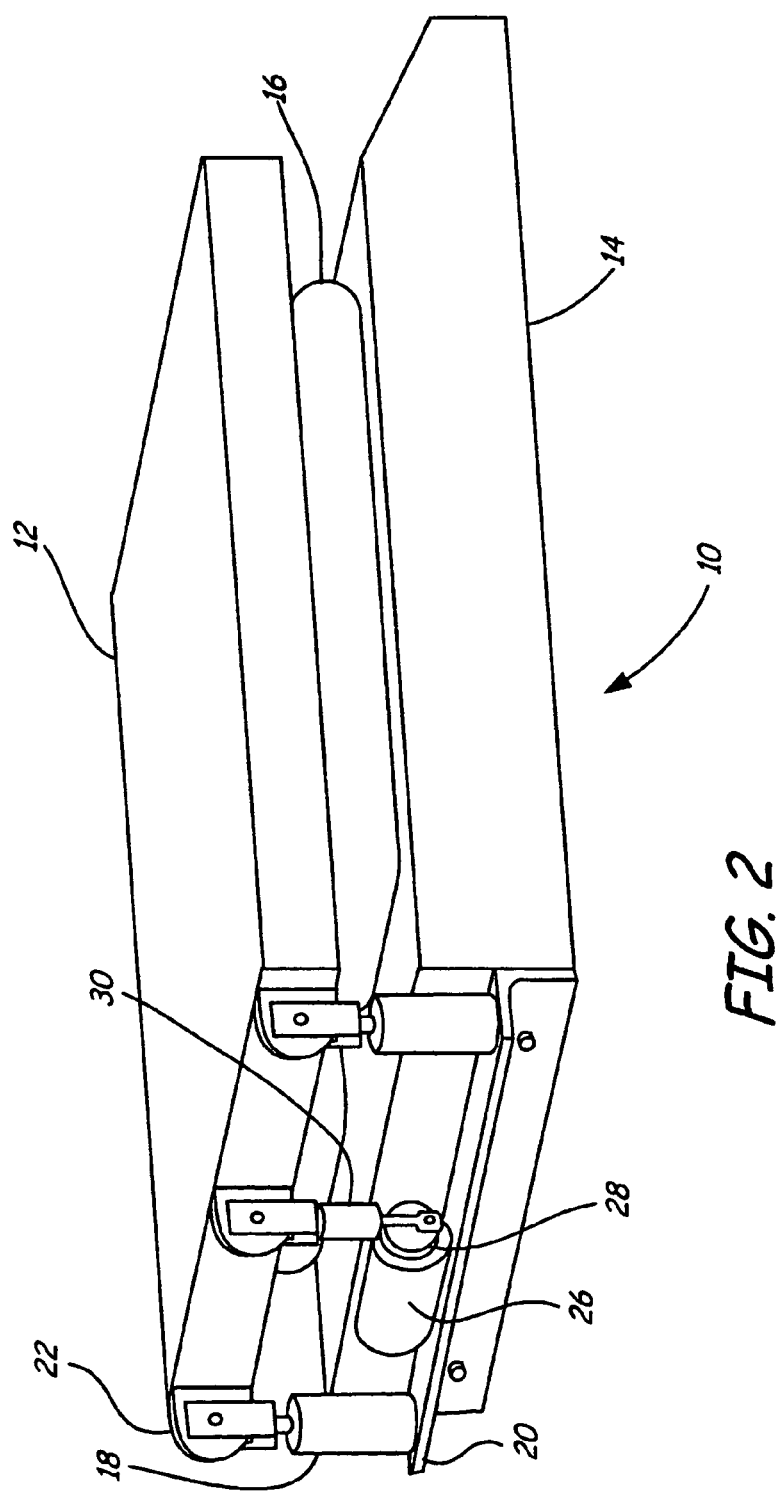
FIG. 2 is a perspective view of the invention from the rear.

FIGS. 1 and 2 show the present thawing apparatus invention 10 with top case 12 and bottom case 14 enclosing and lightly squeezing bags 16 containing frozen biological liquid to be thawed. Also visible in FIG. 1 is one of the spring-loaded hinge supports 18 and adjustable hinge mount 20 which allow invention 10 to accommodate bags of varying thicknesses. Hinge supports 18 are attached to top case 12 by clevis and bracket assembly 22, allowing top case 12 to be opened for insertion or removal of bags 16. The surfaces of top case 12 and bottom case 14 in contact with bags 16 are comprised of heating plates 24, which are preferably heat pipes, either flat or contoured to conform to the shape of bags 16. Temperature of heating plates 24 is controlled by an electronic temperature controller using temperature sensors at or near the surfaces of heating plates 24. A temperature sensor in contact with the surface of the bag being thawed, but insulated from heating plates 24 is used to determine when thawing is complete. Gearmotor 26 acts through crankshaft 28 and spring-dashpot 30 to oscillate top case 12 perpendicular to its surface relative to bottom case 14 and to maintain contact and limit force on bags 16 while oscillations are occurring.

PREFERRED EMBODIMENT—OPERATION

In operation thawing apparatus invention 10 is powered by a grounded power cord being plugged into an a.c. power supply, and controlled by an on-off switch. A bag or bags 16 to be thawed are placed on the surface of bottom case 14 and top case 12 is closed and allowed to rest on bags 16, after which thawing apparatus invention 10 is activated by its on-off switch. Heating plates 24 warm up to their control temperature of about 42 C and gearmotor 26 operates to oscillate top case 12 relative to bottom case 14, at a frequency of 0.5 to 10 Hz, causing mixing of the thawing fluid and increasing heat transfer to bags 16, minimizing thawing time. When thawing is completed, above-freezing temperature is sensed by a thermistor in contact with the thawing bags 16 but insulated from the heating plates 24, and an audible and visual signal notifies the operator of process completion.

OTHER EMBODIMENTS

Hanging Bag Embodiment—Description

Figure 3:
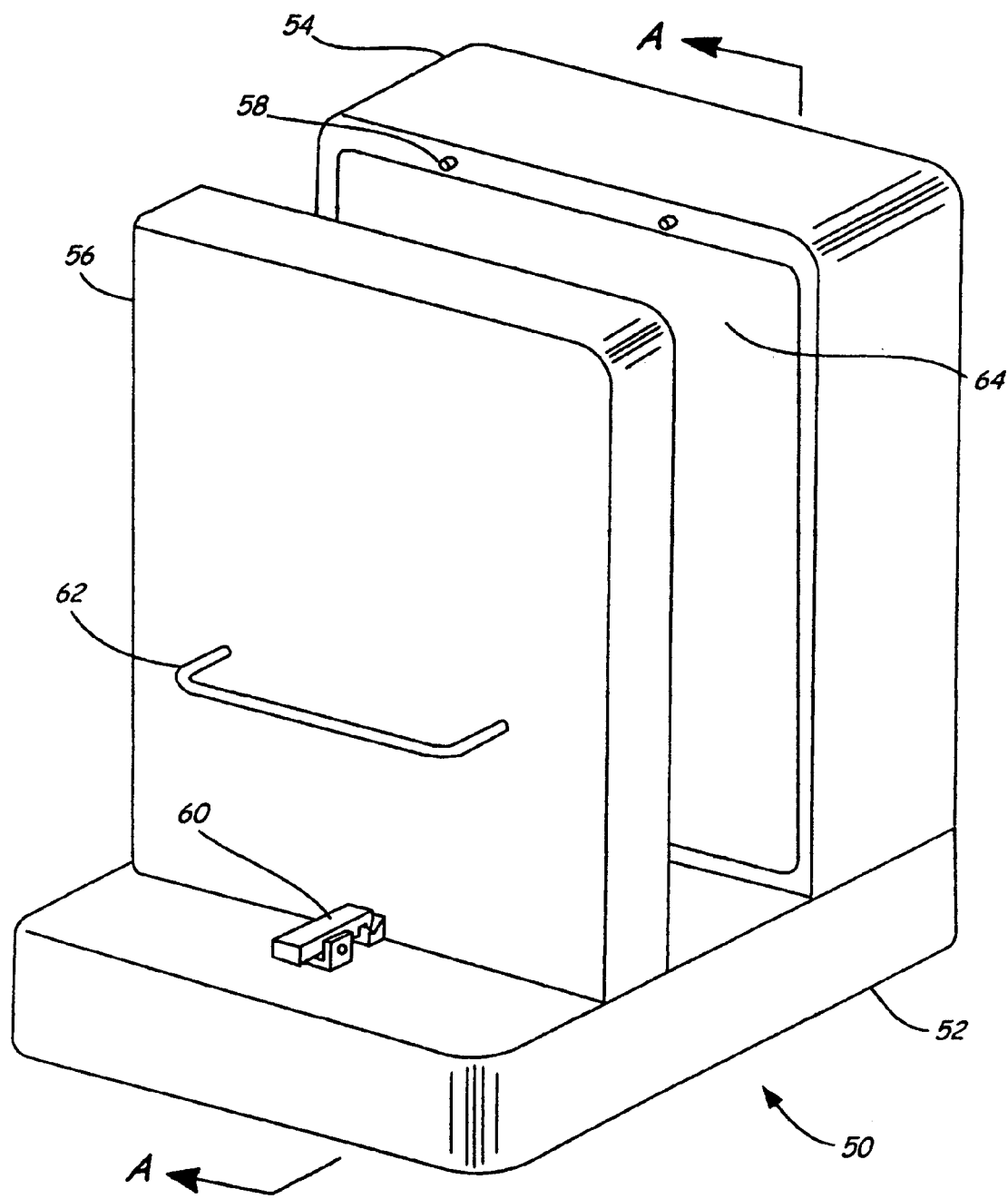
FIG. 3 is a perspective view of another embodiment of the invention.

FIG. 3 shows a hanging bag embodiment 50 of the present thawing apparatus invention with base 52, fixed case 54, movable case 56, bag hanging posts 58, latch 60, opening handle 62 and rear heating plate 64.

Figure 4:
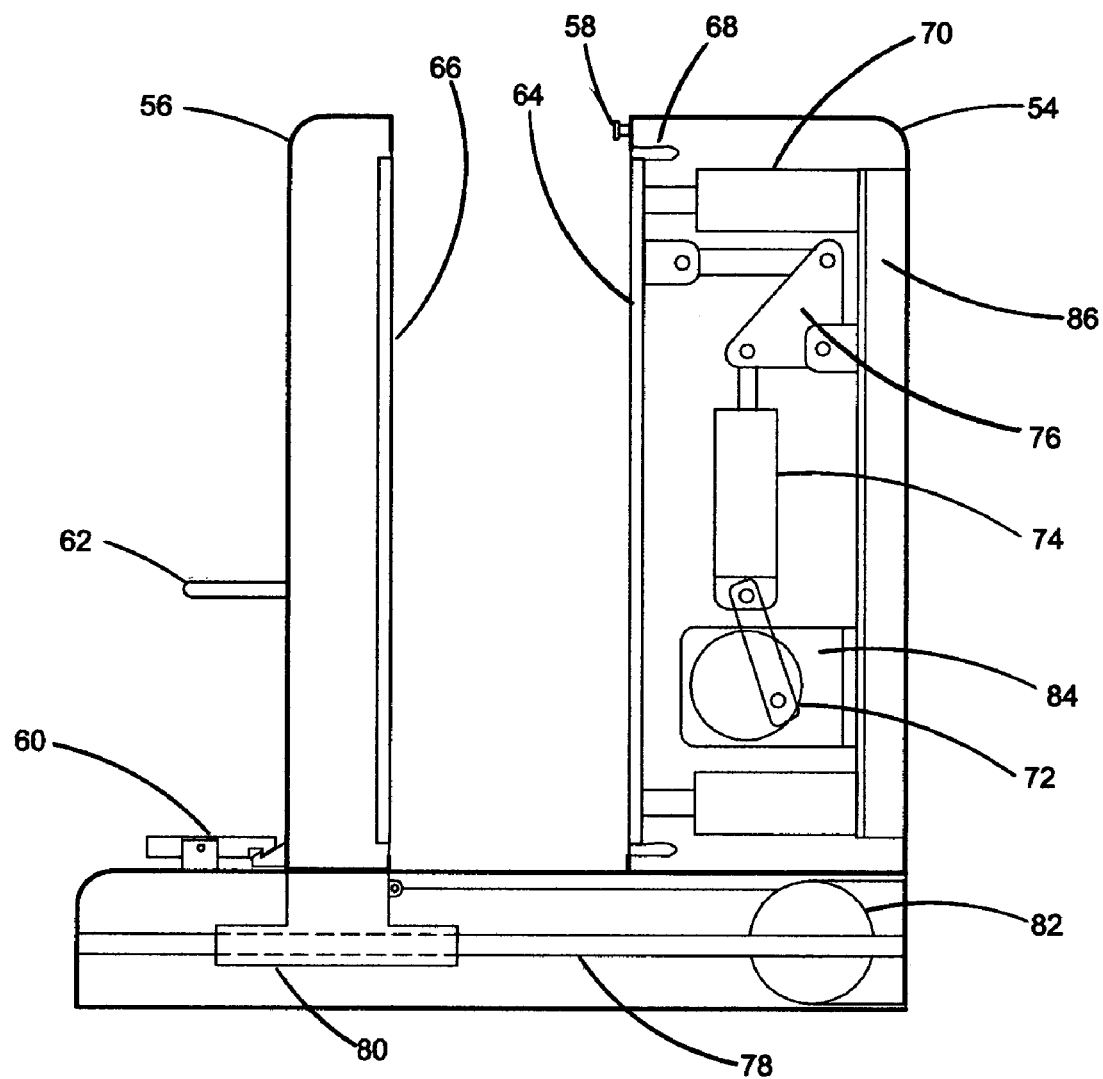
FIG. 4 is a cross-sectional view along A—A of FIG. 3 and in the direction of the arrows.

FIG. 4 shows hanging bag embodiment 50 in cross-sectional view with front heating plate 66, flexural support 68, spring-loaded supports 70, oscillating crank 72, spring-dashpot module 74, bellcrank 76, support rails 78, movable case slider 80, constant force return spring 82, oscillating gearmotor 84, and mounting bracket 86.

Hanging Bag Embodiment—Operation

In operation movable case 56 is opened with opening handle 62 and held in the open position by latch 60. Bag(s) to be thawed are then hung on bag hanging posts 58 and movable case 56 is closed by releasing latch 60. Bag(s) to be thawed are gently held and squeezed between front heating plate 66 and rear heating plate 64 by constant force return spring 82. Movable case 56 is guided by movable case slider 80 sliding on support rails 78. Power is turned on by an on-off switch and front and rear heating plates 66 and 64 warm to about 42 C, beginning the thawing process. Oscillating gearmotor 84 acts through oscillating crank 72, spring-dashpot module 74, and bellcrank 76 to gently oscillate rear heating plate 64 perpendicularly to its surface relative to front heating plate 66 at about 0.5 to 10 Hz, mixing the thawing fluid and enhancing heat transfer. Rear heating plate 64 is flexibly supported in fixed case 54 by flexural support 68 which allows motion only in a direction normal to the heating surface of rear heating plate 64. Heating plate temperature control and sensing of thaw process completion are as in the preferred embodiment.

CONCLUSIONS, RAMIFICATIONS, AND SCOPE

Accordingly, it can be seen that the present invention provides several improvements to biological fluids thawing practice, resulting from novel and unobvious changes in the case of oscillating heating plates and flat heat pipes used as heating plates, eliminating the thermal resistance of extra bags used to isolate thawing bags from water baths in current thawing devices. Additionally, direct contact conductive heating eliminates the thermal resistance of the water boundary layer in water bath devices, increasing heat transfer and reducing thawing time.

Although the description above contains many specificities, these should not be construed as limiting the scope of the invention but as merely providing illustrations of some of the presently preferred embodiments of this invention. Various other embodiments and ramifications are possible within its scope.

Thus the scope of the invention should be determined by the appended claims and their legal equivalents, rather than by the examples given.

What is claimed is:

1. An apparatus for thawing frozen biological fluids utilizing heating plates and oscillatory motion to enhance heat transfer by mixing comprising:
   (A) a first heating plate contacting one generally flat surface of one or more plastic bags containing frozen liquid to be thawed;
   (B) a second heating plate approximately parallel to said first heating plate and contacting the flat surface of said bag(s) opposite said surface contacted by said first heating plate, said heating plates being made of heat conductive material;
   (C) means to hold said bag(s) in position to be thawed;
   (D) means to squeeze said plastic bag(s) to be thawed between said first and second heating plates with a force of about 0.5 to 5 pounds;
   (E) means to apply heat to the back surfaces of said heating plates which are the surfaces opposite the heating surfaces of said heating plates in contact with said bag(s) to be thawed;
   (F) means to sense the temperature of said heating plate heating surfaces where they contact said bag(s) being thawed;
   (G) means to control the temperature of said heating plate heating surfaces at a safe thawing temperature of about 37 to 42 C. where they contact said bag(s) to be thawed;
   (H) means to oscillate one of said heating plates about 0.1 to 0.5 inch relative to said other heating plate at a frequency of about 0.5 to 10 Hz in a direction perpendicular to said heating plate heating surfaces to promote mixing of the thawing fluid;
   (I) means to keep said heating plates in contact with said bags to be thawed and to limit the oscillating force to about 0.1 to 2 pounds while oscillations are occurring;
   (J) means to adjust the spacing of said heating plates to accommodate bags of different thicknesses; and
   (K) means to determine when said frozen liquid is completely thawed,
whereby frozen biological fluids such as blood plasma may be quickly and safely thawed.

2. The apparatus of claim 1 wherein said heating plates are flat.

3. The apparatus of claim 2 wherein said heating plates are flat heat pipes, said heat pipes utilizing internal vapor condensation heating to maintain said heating plate heating surfaces at a controlled isothermal thawing temperature of about 37 to 42 C.

4. The apparatus of claim 1 wherein said heating plates are concavely shaped to approximately conform to the convexly shaped surfaces of said plastic bag(s), providing increased contact area for more efficient heat transfer.

5. The apparatus of claim 4 wherein said heating plates are concavely shaped heat pipes, said heat pipes utilizing internal vapor condensation heating to maintain said heating plate heating surfaces at a controlled isothermal thawing temperature of about 37 to 42 C.

6. The apparatus of claim 1 wherein said heating plates are made of aluminum sheet.

7. The apparatus of claim 1 wherein said means to hold said bag(s) in position to be thawed is gravity, and
   (A) wherein said means to squeeze said plastic bag(s) to be thawed between said first and second heating plates is the weight of the upper heating plate, and
   (B) wherein said means to adjust the spacing of said heating plates to accommodate bags of different thicknesses is an adjustable hinge position,
when said heating plates are horizontal.

8. The apparatus of claim 1 wherein said means to hold said bag(s) in position to be thawed are bag hanging posts when said heating plates are vertical.

9. The apparatus of claim 1 wherein said means to squeeze said plastic bag(s) to be thawed between said first and second heating plates is a constant force spring, and
   (A) wherein said means to adjust the spacing of said heating plates to accommodate bags of different thicknesses is said constant force spring,
when said heating plates are vertical.

10. The apparatus of claim 1 wherein said means to apply heat to said back surraces of said heating plates are etched foil stick-on heaters.

11. The apparatus of claim 1 wherein said means to sense the temperature of said heating plate heating surfaces where they contact said bag(s) being thawed are thermistors.

12. The apparatus of claim 1 wherein said means to control the temperature of said heating plate heating surfaces is an electronic temperature controller.

13. The apparatus of claim 1 wherein said means to oscillate one of said heating plates is a motor-operated bellcrank.

14. The apparatus of claim 1 wherein said means to keep said heating plates in contact with said bag(s) to be thawed is a dashpot in an oscillating linkage.

15. The apparatus of claim 1 wherein said means to determine when said frozen liquid is completely thawed is a thermistor in thermal contact with said bag being thawed but insulated from said heating plate heating surface.

* * * * *